United States Patent [19]

Falk

[11] 3,996,803
[45] Dec. 14, 1976

[54] MOLTEN METAL SAMPLING APPARATUS

[76] Inventor: Richard A. Falk, 519 Westminster Drive, Waukesha, Wis. 53186

[22] Filed: Nov. 26, 1974

[21] Appl. No.: 527,198

[52] U.S. Cl. .................... 73/425.4 R; 73/425.6; 73/425.2

[51] Int. Cl.[2] .................... B01L 3/02; G01N 1/10; G01N 1/14

[58] Field of Search .......... 73/425.4, 425.6, 425.2, 73/425.4 R, 425.4 P, 425.6, DIG. 9; 164/112

[56] References Cited

UNITED STATES PATENTS

| 3,406,736 | 10/1968 | Jett et al. | 73/DIG. 9 |
|---|---|---|---|
| 3,457,790 | 7/1969 | Hackett | 73/DIG. 9 |
| 3,646,816 | 3/1972 | Hance et al. | 73/425.4 R |
| 3,656,350 | 4/1972 | Collins | 73/425.4 R |
| 3,791,219 | 2/1974 | Falk | 73/425.4 R |
| 3,791,220 | 2/1974 | Falk et al. | 73/425.6 |
| 3,798,974 | 3/1974 | Boron | 73/DIG. 9 |
| 3,877,309 | 4/1975 | Hance | 73/DIG. 9 |
| 3,905,238 | 9/1975 | Falk | 73/425.6 |
| 3,913,404 | 10/1975 | Boron | 73/DIG. 9 |

FOREIGN PATENTS OR APPLICATIONS 249,417  3/1963  Germany .................. 73/DIG. 9

Primary Examiner—Richard E. Aegerter
Assistant Examiner—Larry Jones
Attorney, Agent, or Firm—Henry C. Fuller

[57] ABSTRACT

Molten metal sampling apparatus includes a permanent chill mold having opposed mold halves with recesses which define a sample cavity. The permanent mold is protected in use by a disposable housing and fill tube assembly made of paperboard which snugly receives the permanent mold which is fastened to a handle in the form of a pipe. A fibrous refractory gasket is carried by the housing and located against a refractory end wall in the housing to provide a seal when the permanent mold is inserted and pressed against the gasket. Three different fill tube housing assemblies are usable with the permanent mold. One housing assembly is adapted for use as a stream sampler; another for immersion sampling; and a third for pneumatic sampling.

22 Claims, 11 Drawing Figures

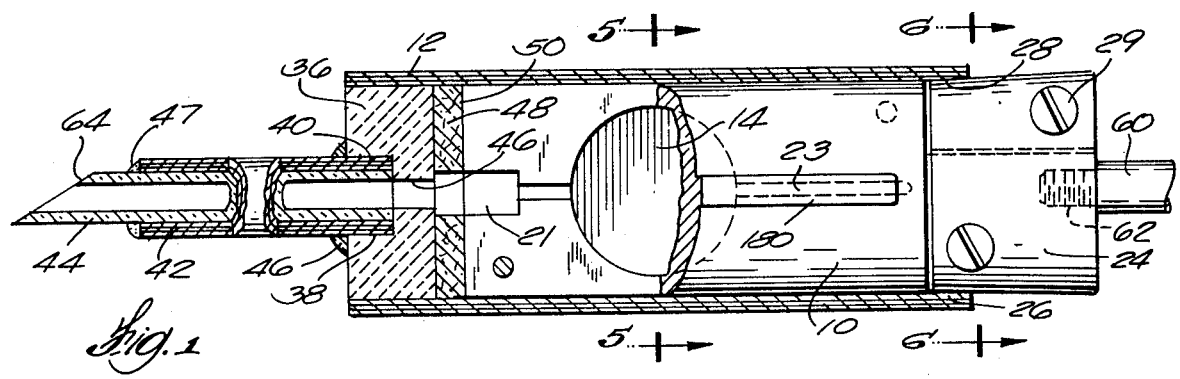
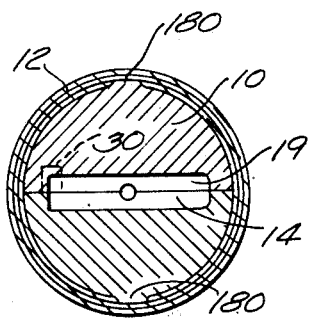
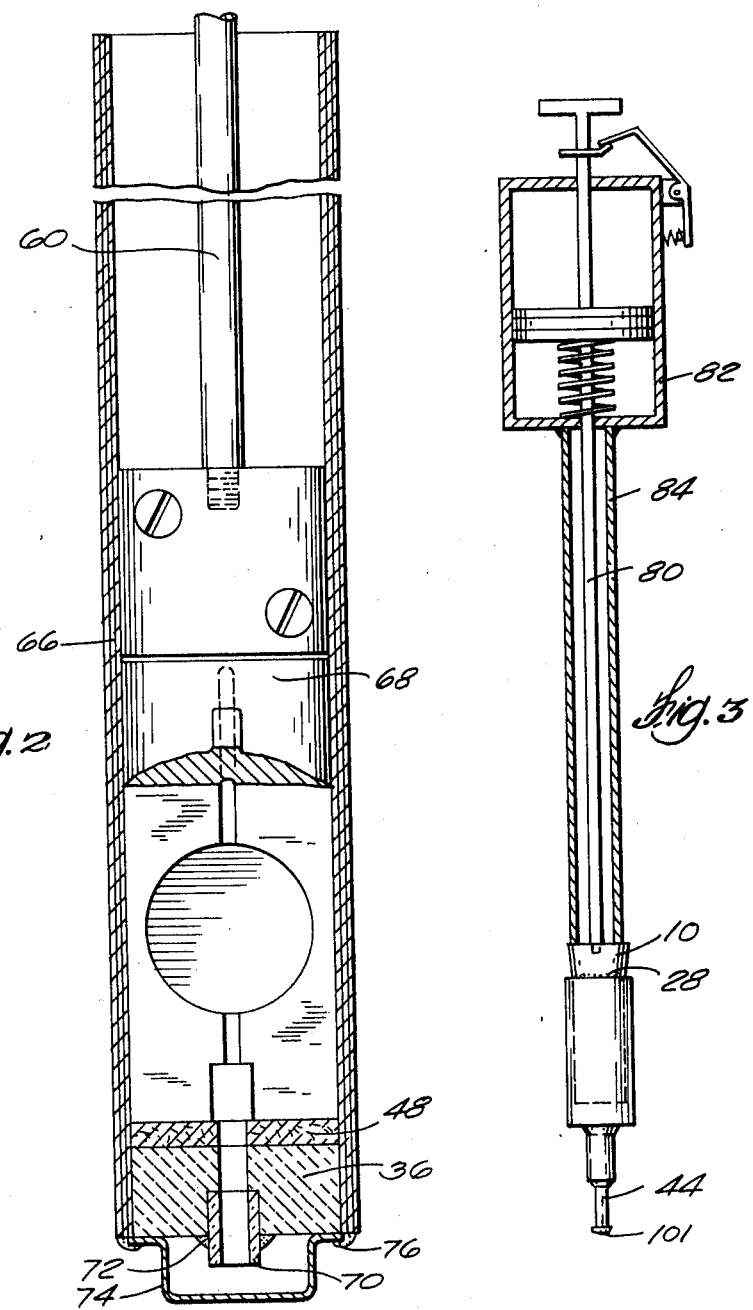
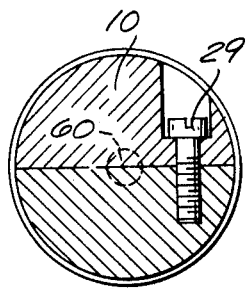

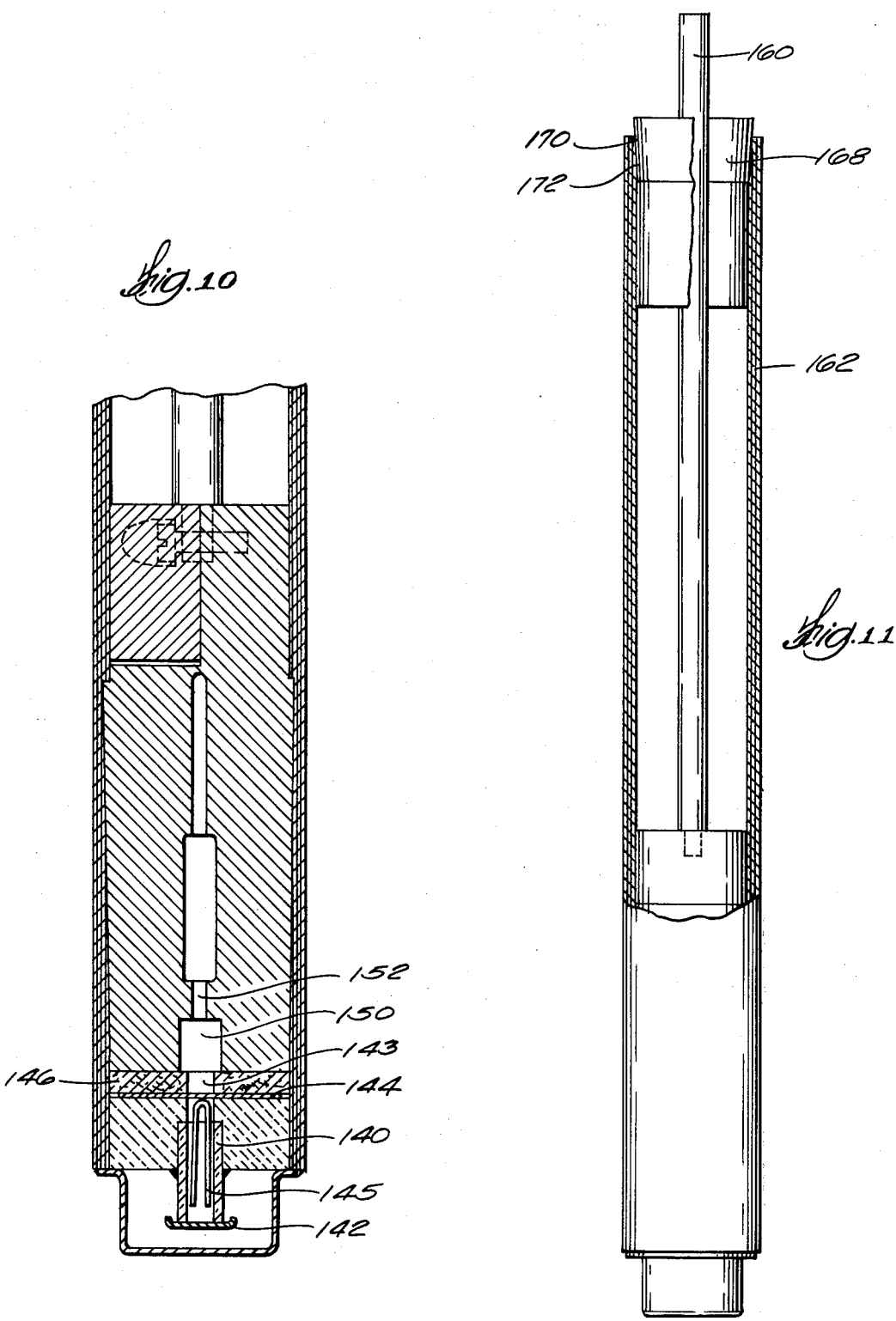

MOLTEN METAL SAMPLING APPARATUS

BACKGROUND OF INVENTION

Various forms of commercially successful samplers have been developed in which a sample cavity is defined by a refractory cartridge or metallic split mold halves. Immersion samplers of this type are shown in my U.S. Pat. No. 3,805,621. Pneumatic samplers are shown in U.S. Pat. No. 3,791,220. A stream sampler is shown in my U.S. Pat. No. 3,,859,857 Both the protective housing and the means defining the sample cavity in the aforementioned patents are disposable and consumable, and used for only one sample. The present invention provides a sampler which utilizes a permanent mold intended for repetitive use which interfits in a disposable housing which also carries a fill tube. Although the cost of the permanent mold is initially higher than the cost of the disposable samplers, expenses are minimized in the long run because the disposable tips and protective housings of the invention cost less than the samplers shown in the aforementioned patents. The stamped steel split molds shown in the foregoing patents are not completely satisfactory for sampling of malleable iron, cast iron, hot steel, aluminum and copper because the tolerances of the molds are quite critical for sampling of these metals.

SUMMARY OF INVENTION

The invention provides a molten metal sampler which in various forms can be used as a stream sampler, immersion sampler, and pneumatic sampler. The permanent mold can be identical for both the stream sampler and the pneumatic sampler with the only difference being a different fill tube. The permanent mold disclosed herein is usable in all types of metal sampling. In the immersion sampler, the protective housing is considerably longer for deep penetration in a bath of molten metal. In the immersion sampler, the housing is also provided with one or two protective fusible caps to prevent entry of slag into the fill tube as the sampler is immersed.

With the pneumatic and stream sampler the mold is provided with a tapered outer surface which interfits with the inner surface of the housing to provide an air seal, which is necessary for pneumatic evacuation of the mold.

The permanent mold is constructed of heavy walled metal of copper or steel and is intended for chill mold sampling. The mold has two mold halves when used to produce one disc and three mold parts for forming two molded discs. The mold parts can be hinged together for convenient retrieving of the sample and to prevent loss of the corresponding mold parts. The recesses in the mold parts which define the mold cavities can be in various sizes or shapes and can include surfaces to form numbers or other indicia to facilitate later correlation of test data with the particular heat.

Tapered ramps on the exterior surfaces of the mold parts press the parts in firm assembly when inserted in the protective paperboard sleeve by engagement with the interior surface of the sleeve to prevent leakage of metal along the mold split line. The protective housing and the sample mold is cylindrical in shape and slidingly interfits into the protective housing. In all embodiments, a handle is attached to the mold which facilitates insertion of the mold into the protective sleeve or housing. In the preferred embodiments, a refractory fiber gasket seals the inner surface of the permanent mold against a refractory end wall in the disposable housing assembly to prevent entry of metal around the end of the permanent mold which would eventually destroy the mold and prevent easy withdrawal of the permanent mold from the housing to retrieve the sample.

Further objects, advantages and features of the invention will become apparent from the following disclosure.

DESCRIPTION OF DRAWINGS

FIG. 1 is a fragmentary sectional view of a stream sampler in accordance with the invention.

FIG. 2 is a fragmentary sectional view of an immersion sampler in accordance with the invention.

FIG. 3 is a sectional view in reduced scale of a pneumatic sampler in accordance with the invention.

FIG. 5 is a sectional view along line 5—5 of FIG. 1.

FIG. 6 is a sectional view along line 6—6 of FIG. 1.

FIG. 10 is a fragmentary sectional view of an additional embodiment of an immersion sampler.

FIG. 11 is a fragmentary sectional view of an immersion sampler with a tapered plug on the handle.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figure 4:
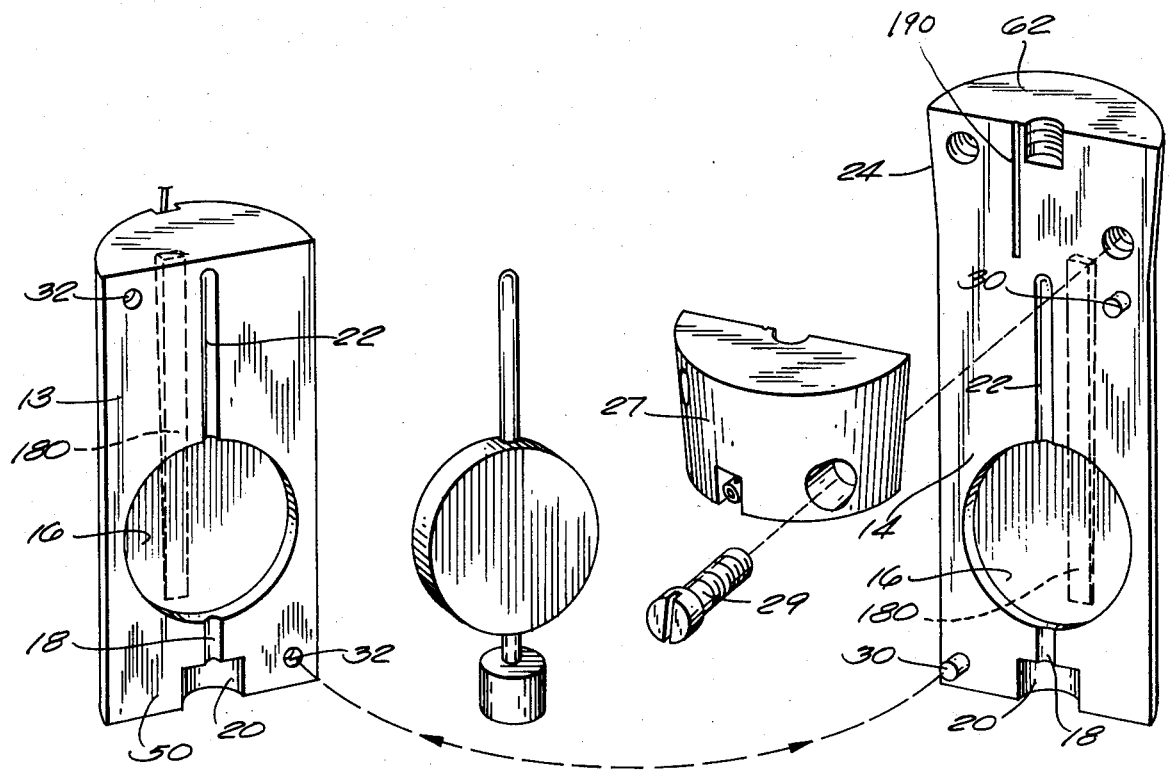
FIG. 4 is an enlarged exploded view of the permanent mold shown in FIGS. 1 and 3, as well as a mold sample formed by the mold cavity.

FIG. 1 shows a stream sampler of the invention which includes a permanent mold 10 contained in a protective housing and fill tube assembly 12. As best shown in FIG. 4, the permanent mold assembly 10 includes mold halves 13 and 14 each containing wall means defining a mold half or recess 16, which together form the sample cavity 19 to mold a disc for spectrographic analysis. The mold parts also contain wall means defining a metal fill passage 18.

The permanent mold halves 13, 14 are also provided with wall means defining recesses 20 which together define a mixing chamber 21 (FIG. 1) which can contain a quantity of aluminum kill for deoxidizing the sample prior to entry into the sample cavity. However, the kill can be contained in the fill tube as subsequently described. The permanent mold can also contain one or more recesses 22 which define a tubular passage 23 to form a pin sample tube for use in an induction furnace carbon analyzer.

The permanent mold 10 shown in FIGS. 1, 3 and 4 is also provided with a tapered surface 24 which, as shown in FIG. 1, interfits in the end wall of the paperboard tubing 26 to provide an air seal and firm engagement. A wax or thermoplastic coating 28 on the inside surface of the tube 26 provides an air seal for the pneumatic sampler shown in FIG. 3 so that the sample cavity 19 can be evacuated.

In FIG. 4, the tapered surface is formed from a semicircular surface portion 24 or mold half 14 and a semicircular portion 27 which is secured to mold half 14 by one or more bolts 29. However, the mold portion 27 can be formed integrally with the mold half 13. The mold halves 13, 14 are provided with locating pins and apertures 30 and 32 to facilitate assembly with the recesses 16 in proper registry. Alternatively, grooves and ribs can be used. The outside diameter of the permanent mold 10 and inside diameter of the protective housing 26 are dimensioned to provide a snug fit of the permanent mold in the tube 26 to thus hold the mold parts in firm assembly.

The protective housing assembly 12 includes a refractory end wall 36 which can be cemented in the tube 26 by refractory cement. The end wall 36 is provided with a counterbore 38 which receives the end 40 of the paperboard sleeve 42 which carries a fused quartz fill tube 44. The tube 42 can be secured to the end wall by refractory cement 46. A bead of refractory cement 47 further anchors the parts together. The fused quartz tube 44 can project inwardly through the end wall or terminate as shown in the counterbore portion 38 in the end wall 36.

In accordance with the invention, sealing means are provided to seal the end surface 50 of the permanent mold 10 against the end wall 36. As disclosed, the sealing means comprises a refractory fiber gasket 48 which is compressible and resistant to temperatures of the molten metal. The gasket 48 prevents metal flow along the end surface 50 which, with repetitive use, could cause damage to the end surface 50 of the permanent mold, and also could impair sampling and provide a mass of metal which would interfere with withdrawal of the mold 10 from the protective housing 26.

In FIG. 1, a rod 60 which forms a handle is threadably received in a threaded aperture 62 in the end of the permanent mold. The handle 60 is utilized to manually manipulate the sampler during use. The handle is also used to insert the permanent mold in the housing 26 and remove the mold from the housing after the sample is taken. In FIG. 1, the fill tube 44 has a beveled tip 64 to facilitate filling of the tube when the sampler is used in a generally horizontal position for taking a sample from a stream. An upturned tip could also be employed.

FIG. 2 shows an immersion sampler 66 which contains a permanent mold 68 similar to that shown in FIG. 4 except that it does not contain a tapered end surface 24. Thus the permanent mold 68 has a cylindrical surface of the same diameter throughout its length and is inserted in the elongated immersion sample tube which may be several feet long, by use of the rod 60. The tube 66 also carries a refractory gasket 48 to seal the sampler 68 against the refractory end wall 36. The immersion sampler is provided with a short, fused quartz fill tube 70 which can be secured by refractory cement 72 to the disc 36. A protective fusible cap 74 is also cemented to the tube by cement 76. The fusible cap prevents entry of molten metal into the fill tube 70 during immersion of the sampler through the slag in a molten metal bath.

In FIG. 3, a pneumatic sampling apparatus 80 is disclosed which is similar to the sampling apparatus shown in FIG. 1 except that a pneumatic device 82, as shown and described in U.S. Pat. No. 3,791,220, is connected to a pipe 84 which is threadably connected to a permanent mold 10. In addition, the fill tube 44 need not be provided with a beveled end 64. It can be provided with a fusible cap 101. The permanent mold is also provided with an air passage 190 (FIGS. 4, 5) to afford air evacuation of the mold upon actuation of the pneumatic device 82.

Figure 7:
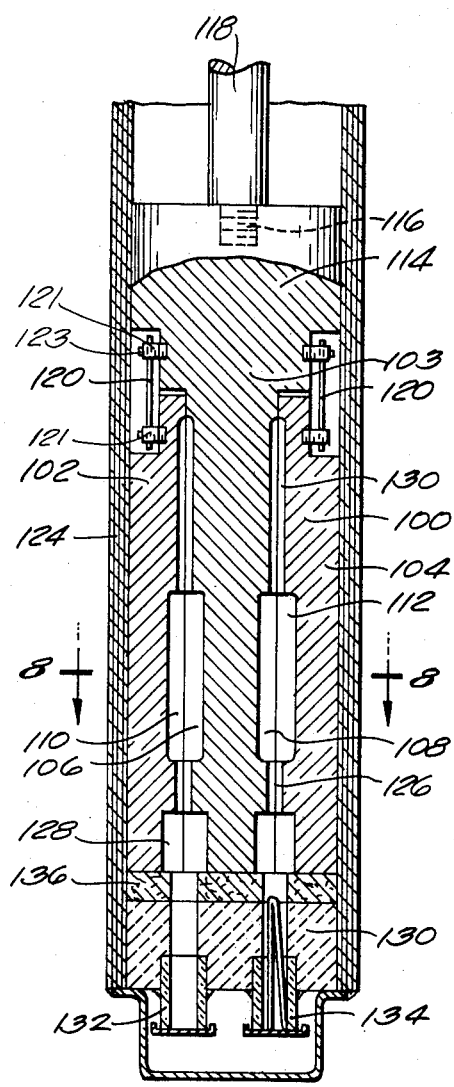
FIG. 7 is a fragmentary sectional view of a modified embodiment of an immersion sampler.
Figure 8:
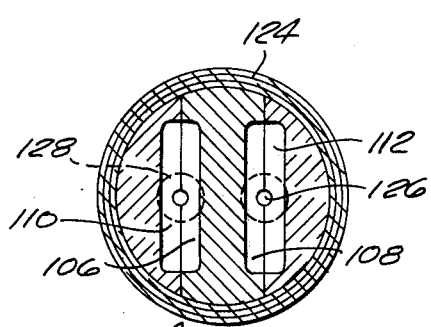
FIG. 8 is a sectional view along line 8—8 of FIG. 7.

FIGS. 7 and 8 show an immersion sampler in which the reusable mold 100 comprises a first part 102, a second part 103, and a third part 104. Mold part 103 is located intermediate parts 102 and 104 and is provided with recesses 106 and 108 on opposite faces of part 103 which cooperate with recesses 110 and 112, respectively, on parts 102 and 104 to define mold cavities. Mold part 103 is integral with mold part 114 which has a threaded aperture 116 for receiving a handle 118. Mold parts 102 and 104 are hinged to mold part 114 by hinges or flexible cables 120. The cable 120 can have ends received in apertures in pegs 121. Screws 123 in the ends of the pegs engage and clamp the cable. The cables and screws are desirably located in recesses so that the cables do not project beyond the outline of the mold parts and interfere with insertion and withdrawal of the sampler from the protective housing 124. The reusable mold parts of the sampler shown in FIG. 7 are also provided with cooperating recesses, inlet passages 126, mixing chambers 128 and pin sample passages 130.

The fill tube assembly of the FIG. 7 embodiment also includes a refractory wall or disc 130 which carries fused quartz fill tubes 132 and 134 and a sealing gasket 136.

FIG. 10 shows an immersion sampler in which the fill tube 140 is provided with a fusible or heat-destructible cover 142 at one end and a destructible sealing member 144 at the other end to positively locate aluminum kill 145 within the passage 147 formed by the tube 140, the aperture 141 in the disc 130, and the aperture 143 in the gasket 146. The kill as disclosed is in the form of a wire which thus is prevented from shifting from the position of FIG. 10 into the mixing chamber 150 of the permanent mold or the fill passage 152 of the permanent mold. Pre-measured quantities of kill can be provided for various customers' requirements with the kill in the same position to provide uniform samples.

Figure 9:
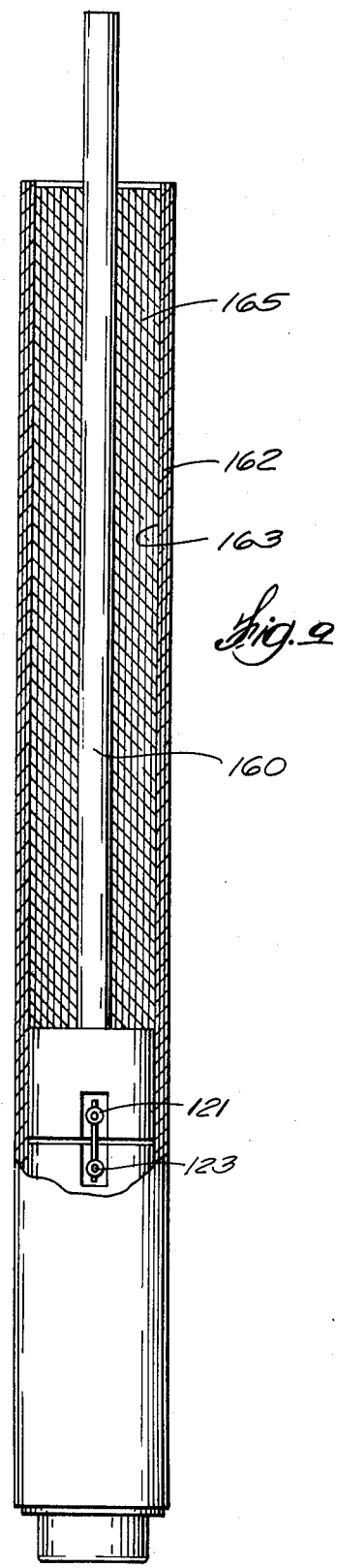
FIG. 9 is a view in fragmentary section of a further embodiment of an immersion sampler.

With immersion samplers such as shown in FIGS. 2, 9 and 11, the protective housing 162 may be 3 feet in length. To prevent displacement between the handle 160 and the housing 162, means are provided on the handle 160 and engageable with the inner surface 163 of the tube 162. As disclosed in FIG. 9, the handle 160 is provided with a thick walled paperboard tube 165 which is fixed to the rod 160 and which slides in the interior of the tube 162 to securely anchor the rod or handle 160 in the upper end of the tube 162. In FIG. 11, a plug 168 is affixed to the handle 160 and is provided with an exterior tapered surface 170 which engages the end 172 of the housing 162.

As best shown in FIGS. 4 and 5 the exterior of the reusable mold can be provided with ramps 180 which are tapered downwardly and inwardly toward the mold fill passage 18 to provide a snug, secure fit in the housing 12. The ramps 180 are located opposite the split line of the molds to press the mold halves together during assembly in the housing.

Inasmuch as the permanent mold is reusable indefinitely, the user of the sampler only needs a supply of the consumable protective housing and fill tube assemblies which do not contain any mold. Thus, the cost of the sampling apparatus is considerably less than a sampler in which the mold is discarded after each sample is taken as with the commercial production samplers shown in the foregoing patents.

In addition, the use of the permanent chill mold in the sampling apparatus of the invention provides samples superior for spectrographic analysis. Chill molds cannot be used in quantity in the samplers shown in my previous patents because of the considerable expense involved.

I claim:

1. Molten metal sampling apparatus comprising a reusable mold comprising a plurality of opposed mold parts having wall means defining a sample cavity and a sample inlet passage and said parts being hinged together for movement between a closed position for sample formation and an open position for sample retrieval, and including a disposable housing and fill tube assembly sized to snugly receive said mold and retain said mold parts in registry during sample formation.

2. Sampling apparatus in accordance with claim 1 including longitudinally extending projections on said mold parts engageable with said disposable housing.

3. Molten metal sampling apparatus comprising a reusable mold having separable mold parts with recesses defining a mold cavity, a consumable fill tube and housing assembly having a protective housing with an end wall forming an abutment and an interior sized to receive said mold parts and compressible refractory fiber sealing means to seal said reusable mold to said housing end wall abutment and provide a sealed flow passage between said fill tube assembly and said reusable mold when said mold is inserted in said protective housing.

4. Molten metal sampling apparatus comprising a reusable mold comprising a plurality of opposed mold parts having wall means defining a sample cavity and a sample inlet passage and said parts being hinged together for movement between a closed position for sample formation and an open position for sample retrieval, and including a disposable housing and fill tube assembly sized to snugly receive said mold and retain said mold parts in registry during sample formation and wherein said reusable mold includes first, second and third mold parts, with said second part being located intermediate said first and third parts, and wherein said second part has wall surfaces defining recesses on opposite faces of said second part which cooperate with wall means defining recesses in said first and third parts to define two mold cavities, and wherein said fill tube assembly has fill tubes for each of said two mold cavities.

5. Molten metal sampling apparatus comprising a reusable sample mold having wall portions defining a sample cavity, wall means defining a sample inlet passage in communication with said cavity, said reusable mold having an end surface through which said sample inlet passage is open, and including a disposable fill tube assembly connectable with said reusable mold during use, said fill tube assembly including a housing, wall means in said housing defining a fill passage, communicating with the inside of said housing, and wherein said mold is sized to be received in said housing with registry of said inlet passage and said fill passage for communication of said inlet passage and said fill passage, and sealing means in the form of a compressible and heat resistant gasket disk between said mold and said fill tube passage to seal the mold end surface in said housing said gasket having an aperture to provide a continuous flow path through said fill passage into said sample mold and prevent metal flow around said end surface of said reusable mold adjacent said sample inlet passage and afford separation of said fill tube assembly and said mold when a sample is obtained and wherein said disposable fill tube assembly has a fill tube with a beveled tip for use as a stream sampler, and wherein said fill tube assembly includes a paperboard sleeve which supports said fill tube.

6. Molten metal sampling apparatus comprising a reusable sample mold having wall portions defining a sample cavity, wall means defining a sample inlet passage in communication with said cavity, said reusable mold having an end surface through which said sample inlet passage is open, and including a disposable fill tube assembly connectable with said reusable mold during use, said fill tube assembly including a housing, rigid wall means at one end of said housing defining an abutment and a fill passage, said fill passage communicating with the inside of said housing, and wherein said mold is sized to be received in said housing with registry of said inlet passage and said fill passage for communication of said inlet passage and said fill passage, and sealing means in the form of a compressible and heat resistant gasket disk between said mold and said abutment said gasket having an aperture to provide a continuous flow path through said fill passage into said sample mold and seal the mold end surface in said housing and prevent metal flow around said end surface of said reusable mold adjacent said sample inlet passage when said mold is in said housing and said gasket is compressed against said abutment and afford separation of said fill tube assembly and said mold when a sample is obtained.

7. The sampling apparatus of claim 6 wherein said reusable mold comprises two opposed parts and wall means in each of said opposed parts which cooperate to define the sample cavity and sample fill passage.

8. The sampling apparatus of claim 7 including locating pegs on one of said opposed parts, and apertures on the other of the mold parts which are registrable with said pegs to orient the mold halves.

9. The sampling apparatus of claim 7 wherein said housing and said mold are sized to provide a snug fit upon insertion of said mold parts in said housing to retain the mold halves in assembly during use.

10. The sampling apparatus of claim 6 wherein said mold is provided with a tapered end portion which is engageable with the inner surface of said housing to provide an air seal.

11. The sampling apparatus of claim 6 including a chamber in said mold communicating with said mold inlet passage and kill in said chamber for deoxidizing said sample.

12. The sampling apparatus of claim 6 wherein said gasket is formed from refractory fiber.

13. The sampling apparatus of claim 6 wherein said handle is threadably attached to said permanent mold.

14. The sampling apparatus of claim 1 including a pipe connected to and in communication with said mold and including means for evacuating the sample cavity connected to said pipe for pneumatic withdrawal of molten metal into said sample cavity.

15. The sampling apparatus of claim 6 wherein said fill tube assembly includes a fusible closure over said fill tube entrance to prevent entry of slag into said tube during immersion into a molten metal bath.

16. The sampling apparatus of claim 15 wherein said housing extends a substantial distance from said mold to prevent contact of said handle with the bath of molten metal.

17. Sampling apparatus in accordance with claim 6 wherein said mold is made from metal and has relatively thick walls to provide a chill sample.

18. Sampling apparatus in accordance with claim 6 wherein said housing is a paperboard sleeve.

19. Sampling apparatus in accordance with claim 6 wherein said gasket is carried by said fill tube and housing assembly.

20. Molten metal sampling apparatus in accordance with claim 1 wherein said mold parts have tapered surfaces engaging said housing at the end of said housing remote from said fill tube and provides a snug fit of said mold and said housing and a handle connected to said mold parts to afford manipulation of said mold and fill tube and housing assembly together.

21. Sampling apparatus in accordance with claim 1 including a quantity of kill located in said fill tube and destructible means at opposite ends of said fill tube to positively position said kill in said fill tube in advance of said sample cavity.

22. Molten metal sampling apparatus in accordance with claim 1 including handle means connected to said reusable mold for manipulating and inserting said reusable mold in said housing assembly, and including spacer means on said handle remote from said permanent mold for engaging the inside surface of said housing to prevent displacement of said handle with respect to said housing during manipulation of said apparatus.

* * * * *